(12) United States Patent
Zoeller, III

(10) Patent No.: US 8,049,878 B2
(45) Date of Patent: Nov. 1, 2011

(54) SYSTEMS AND METHODS FOR DETECTING DEFECTS IN CERAMIC FILTER BODIES

(75) Inventor: Leon Robert Zoeller, III, Hammondsport, NY (US)

(73) Assignee: Corning Incorporated, Corning, NY (US)

( * ) Notice: Subject to any disclaimer, the term of this patent is extended or adjusted under 35 U.S.C. 154(b) by 97 days.

(21) Appl. No.: 12/196,600

(22) Filed: Aug. 22, 2008

(65) Prior Publication Data
US 2010/0045975 A1 Feb. 25, 2010

(51) Int. Cl.
*G01N 21/00* (2006.01)
(52) U.S. Cl. .................... 356/237.6; 356/237.1
(58) Field of Classification Search .... 356/237.1–237.6, 356/241.1
See application file for complete search history.

(56) References Cited

U.S. PATENT DOCUMENTS

| | | | |
|---|---|---|---|
| 3,826,923 A | 7/1974 | Trimble et al. | |
| 4,319,840 A | 3/1982 | Kondo et al. | |
| 5,102,434 A | 4/1992 | Hijikata et al. | |
| 5,419,181 A | 5/1995 | Egan et al. | |
| 5,463,462 A * | 10/1995 | Ohnishi et al. | 356/521 |
| 5,548,400 A * | 8/1996 | Bourguinat | 356/241.1 |
| 6,414,752 B1 | 7/2002 | Sullivan et al. | |
| 6,452,670 B1 | 9/2002 | Bour et al. | |
| 6,605,807 B2 | 8/2003 | Safai | |
| 6,819,418 B2 * | 11/2004 | Yoneda | 356/237.6 |
| 7,043,998 B2 | 5/2006 | Werve | |
| 7,366,340 B1 * | 4/2008 | Smithgall | 382/141 |
| 7,701,570 B2 * | 4/2010 | Gargano et al. | 356/237.6 |
| 2003/0112437 A1 * | 6/2003 | Enomoto et al. | 356/402 |
| 2003/0174320 A1 * | 9/2003 | Yokoyama et al. | 356/237.6 |
| 2004/0223638 A1 | 11/2004 | Lespinet et al. | |
| 2006/0133563 A1 * | 6/2006 | Hopkins et al. | 378/5 |
| 2007/0091309 A1 * | 4/2007 | Kondo | 356/364 |

(Continued)

FOREIGN PATENT DOCUMENTS

JP 2005274179 A 6/2005

(Continued)

OTHER PUBLICATIONS

EP Translation of Patent Abstracts of Japan 2005274179.

*Primary Examiner* — Hoa Pham
(74) *Attorney, Agent, or Firm* — Timothy M. Schaeberle

(57) ABSTRACT

Systems (50) and methods are disclosed for detecting defects (DEF1-DEF5) in a ceramic filter body (10) having a honeycomb structure (12) that defined multiple channels (20). Plugs (30) are used to seal select channel ends (22, 24). The methods include using a first light source unit (52) and a first detector unit (62) operably arranged at respective first and second ends (16, 18) of the honeycomb structure so as to be capable of being in optical communication. Light beams (LB) are transmitted from the first light source unit to the first detector unit through multiple channels. Defects in a given plug allow a detectable portion (LBD) of the corresponding light beam to be detected. Multiple detector elements (64) are used to detect the detectable light beam portion to provide location and intensity variation information, which helps deduce the precise location and nature of the defect. Light source units (52, 52') at opposite ends (16, 18) and detector units (62, 62') at opposite ends (18, 16) form a "double-ended" system that allows for the simultaneous measurement of defect at both ceramic filter body ends. Systems and methods for measuring defects (DEF4, DEF5) for unplugged ceramic filter bodies are also disclosed.

20 Claims, 12 Drawing Sheets

U.S. PATENT DOCUMENTS

| | | |
|---|---|---|
| 2007/0132988 A1 | 6/2007 | Gargano et al. |
| 2007/0266789 A1* | 11/2007 | Hampton et al. ............... 73/596 |
| 2008/0115597 A1 | 5/2008 | Ohno et al. |
| 2008/0225302 A1* | 9/2008 | Nagatoshi et al. ............ 356/601 |
| 2009/0223293 A1* | 9/2009 | Owens ............................ 73/620 |
| 2009/0237652 A1* | 9/2009 | Akao et al. ................. 356/237.1 |

FOREIGN PATENT DOCUMENTS

| | | |
|---|---|---|
| WO | 2006019446 A2 | 2/2006 |
| WO | 2007070318 | 6/2007 |
| WO | 2007126692 | 4/2008 |

* cited by examiner

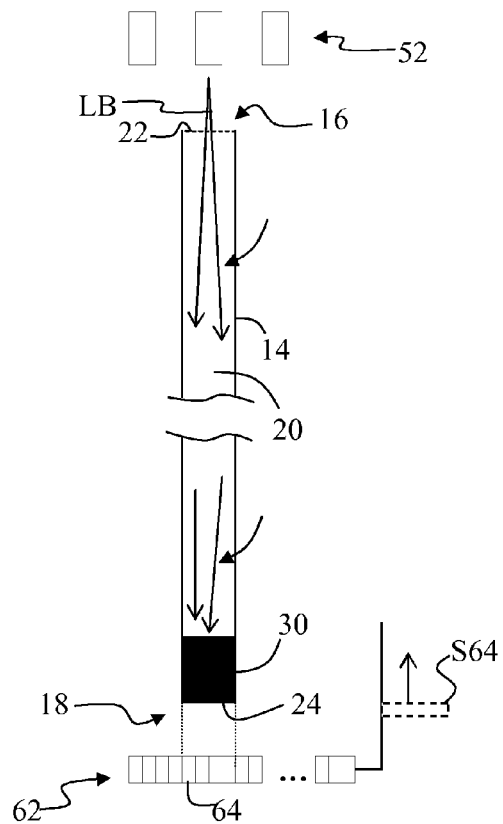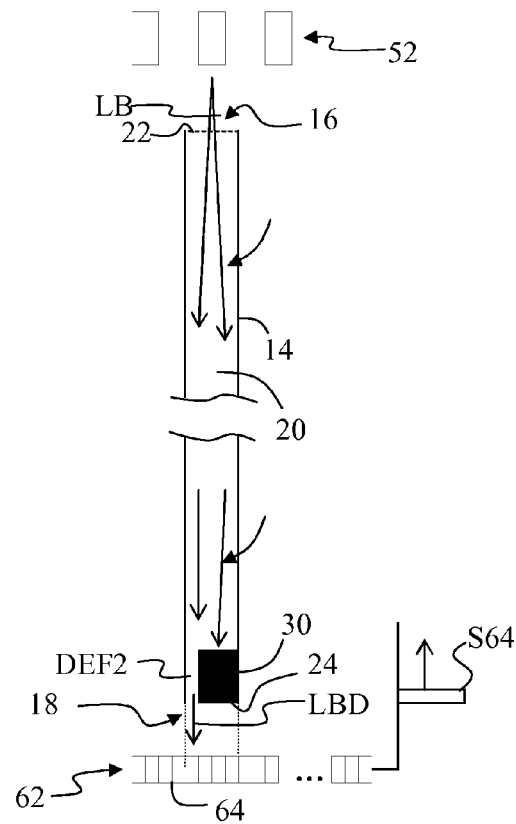
FIG. 10A    FIG. 11A
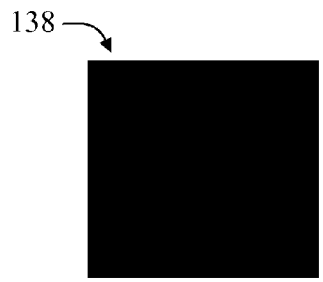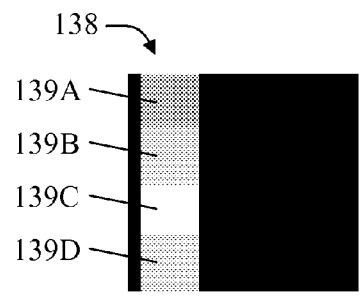
FIG. 10B    FIG. 11B

SYSTEMS AND METHODS FOR DETECTING DEFECTS IN CERAMIC FILTER BODIES

FIELD

The present invention relates to ceramic-based filters, and in particular relates to systems and methods for detecting defects in the ceramic filter bodies used to make such filters.

BACKGROUND

Ceramic bodies having internal honeycomb structures defined by porous walls have several uses, e.g., as solid particulate filter bodies and as stationary heat exchangers. Such uses require selected channels of the structure to be sealed or plugged by manifolding and the like at one or both of the respective ends thereof.

In the operation of a ceramic plugged filter, a contaminated fluid or gas is brought under pressure to an inlet face and enters the ceramic filter body via those channels with open ends at the inlet face. Because these channels are sealed at the opposite (outlet) face, the contaminated fluid is forced through the thin porous walls into adjoining channels. The solid particulate contaminant in the fluid, which is too large to pass through the porous openings in the walls, is left behind, and a cleansed fluid exits the filter through the outlet channels.

Sealing the channels involves inserting a plugging material into the open ends of select channel channels, and subsequently drying the plugged filter. Previous methods for forming a plugged honeycombed structure include forming an extruded ceramic-based green honeycomb structure, drying the structure in an oven, plugging the open ends of select channels, and firing the resultant plugged honeycomb structure.

The plugging methods can potentially lead to defects in the plugs, which cause filter leaks. The channels of the honeycomb structure can also be obstructed within the ceramic filter body itself due to the collapse of a channel wall, or if excess material remains in the channels. It is therefore important in the filter manufacturing process to be able to quickly and efficiently inspect the ceramic filter bodies for defects that could ultimately cause leaks in the subsequently formed filter.

SUMMARY

One aspect of the invention is a method of detecting defects in a ceramic filter body having a honeycomb structure with first and second ends and an array of longitudinal channels between the first and second ends. The method includes positioning a first light source unit having at least one first light source element, and a first detector unit having at least one first detector element to be adjacent the first and second ends, respectively, so that the at least one first light source element and the at least one first detector element are capable of being in optical communication through a corresponding at least one first channel. The method also includes transmitting at least one first light beam from the first light source unit to the first detector unit through the at least one first channel. The method further includes detecting first light from the at least one first light beam with the at least one first detector element and, in response thereto, generating at least one first electrical detector signal representative of the detected first light. The method additionally includes processing the at least one first electrical detector signal to determine if there is at least one first defect within the at least one first channel.

Another aspect of the invention is a system for detecting defects in a ceramic filter body having a honeycomb structure with first and second ends and an array of longitudinal channels between the first and second ends. The system includes a first light source unit having at least one first light source element and positioned adjacent the first honeycomb structure end, the light source unit adapted to generate a first light beam. The system also includes a first detector unit having at least one first detector element. The first detector unit is positioned adjacent the second honeycomb structure end so that the at least one first light source element and the at least one first detector element are capable of being in optical communication through a corresponding at least one first channel. The first detector unit is configured to generate first electrical detector signals in response to detecting first light from the first light beam. The system also includes a processor electrically connected to the first detector unit. The processor is adapted to process the first electrical detector signals to determine if there is at least one first defect within the at least one first channel.

Another aspect of the invention is a method of detecting defects in a ceramic honeycomb structure having first and second ends and an array of longitudinal channels having first and second channel ends, and ideally having first and second plugs at select first and second channel ends so as to seal the select channel ends. The method includes transmitting first light through the first end to the second end through one or more first channels and detecting at the second end first light that passes through at least one first defect. The method also includes transmitting second light through the second end to the first end through one or more second channels and detecting at the first end second light that passes through at least one second defect. The method also includes processing the first detected light and the second detected light so as to detect the at least one first defect and the at least one second defect.

These and other advantages of the invention will be further understood and appreciated by those skilled in the art by reference to the following written specification, claims and appended drawings.

BRIEF DESCRIPTION OF THE DRAWINGS

FIG. 10A is a close-up view of a single ceramic filter body channel and shows the light beam traveling in the channel and being blocked by a defect-free plug so that no light is incident upon any of the detector elements in the linear detector unit;

FIG. 10B is the channel end image formed by the detector unit in the defect-free case of FIG. 10A;

FIG. 11A is similar to FIG. 10A, but shows the case where there is a plug defect so that a detectable portion of the light beam passes through the defect and is incident upon and detected by one or more of the detector elements;

FIG. 11B is similar to FIG. 10B, but shows in gray scale the location and distribution of the detected light relative to the channel end;

DETAILED DESCRIPTION

Reference is now made in detail to the present example embodiments of the invention, examples of which are illustrated in the accompanying drawings. Whenever possible, the same or similar reference numbers and symbols are used throughout the drawings to refer to the same or similar parts.

Figure 1:
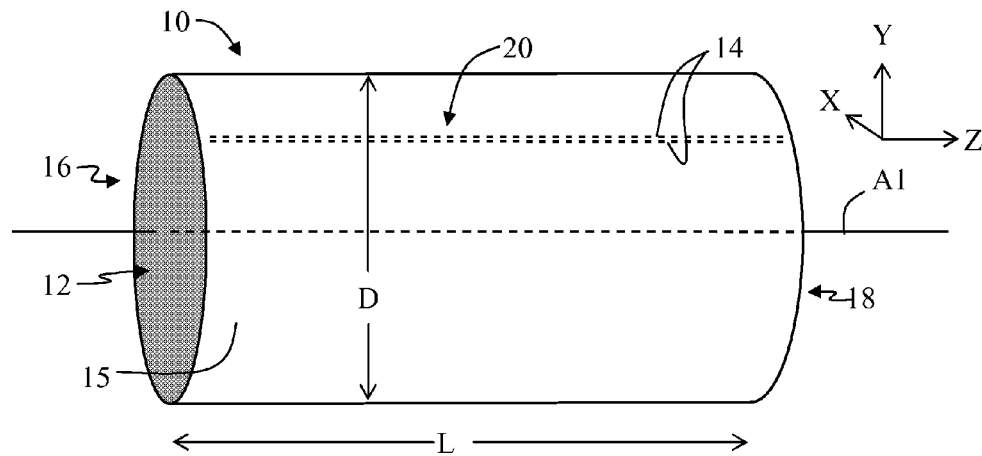
FIG. 1 is a perspective view of an example unplugged ceramic filter body.

FIG. 1 is a perspective view of an unplugged example ceramic filter body 10. Ceramic filter body 10 has a honeycomb structure 12 having an axial length L and a central axis A1 that defines an axial (longitudinal) direction. Cartesian coordinates are provided for the sake of reference.

Honeycomb structure 12 is defined by a matrix of intersecting, thin, porous walls 14 surrounded by an outer wall 15. Walls 14 extend across and between opposing ends 16 and 18 and form a large number of adjoining hollow passages or "channels" 20 that also extend between ends 16 and 18 and that have respective channel ends 22 and 24 thereat (see FIG. 5A). Ceramic filter body 10 can have, for example, between 100 to 900 channels per square inch. In an example embodiment, walls 14 are typically rendered quite thin, e.g., on the order of 2-10 mils thick, or even 2-6 mils thick. In an example embodiment, ceramic filter body 10 can have a diameter D in the range from 3" to 17".

Ceramic filter body 10 is manufactured, for example, by extruding a plasticized ceramic-forming precursor of cordierite, mullite, silicon carbide, or aluminum titanate through an extrusion die. The extruded "green body" is then cut and dried. Such green bodies are quite fragile and must be transported to a kiln, where the resultant heat transforms the relatively soft and fragile green body into hardened, fired ware having a rigid honeycomb structure 12.

Figure 2:
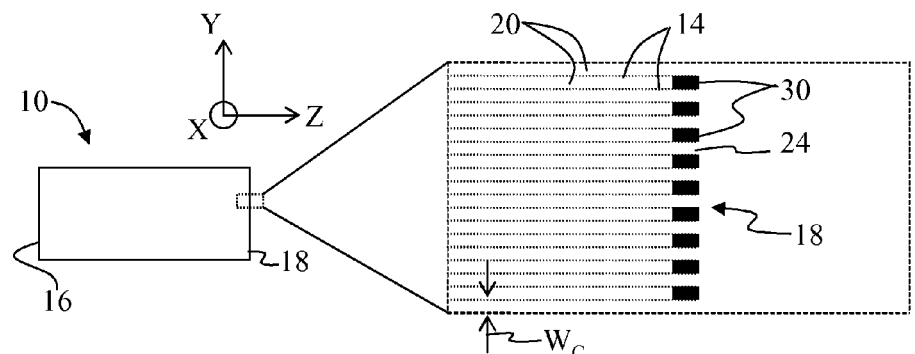
FIG. 2 includes a distant side view of a ceramic filter body, along with a close-up Y-Z cross-sectional inset view of an end portion of the ceramic filter body that shows how the plugs are arranged in alternate channel ends.

FIG. 2 includes a distant side view of ceramic filter body 10 and a close-up Y-Z cross-sectional inset view of an end portion at end 18 of the ceramic filter body that shows how plugs 30 are arranged in alternate channel ends 24 at end 18. Channel ends 22 and 24 are initially open (channel end 22 not shown in FIG. 2; see FIG. 5B). Plugs 30 are formed in channel ends 22 or 24 of each channel 20, usually in an alternating pattern so that each ceramic filter body end 16 and 18 has a "checkerboard" pattern of plugs shifted by one channel relative to the other body end so that each channel only has one plugged end. Ideally, each channel 20 is completely open at one end 16 or 18 and is perfectly sealed by a plug 30 at its other end, and channel 20 is perfectly clear (i.e., completely unobstructed). Channels 20 have a channel width $W_C$.

Figure 3:
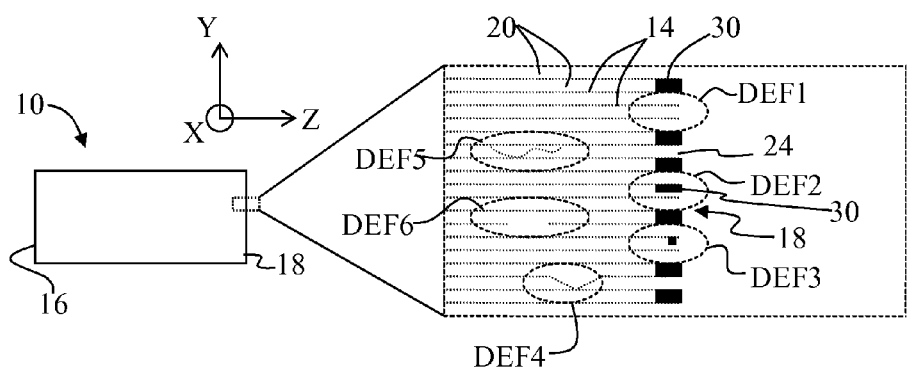
FIG. 3 is similar to FIG. 2, but shows five different examples of defects associated with the ceramic filter body that can lead to filter leaks.

As discussed above, the filter manufacturing processes, including the plugging methods use to selectively plug the channel ends, can potentially lead to defects that can result in leaks or reduced performance when the plugged ceramic filter body is used as a filter. FIG. 3 is similar to FIG. 2, but shows five example manufacturing defects DEF that can result in filter leaks. A first type of defect, denoted by DEF1, is where one of the plugs 30 is entirely missing. A second type of defect, denoted by DEF2, is where plug 30 is partially present, i.e., it has the correct axial depth, but does not have sufficient width to plug the entire channel 20. A third type of defect, denoted by DEF3, is similar to defect DEF2, but the axial depth is off so that only a small portion of plug 30 is present. These defects are referred to herein as "plug" defects. Other types of plug defects, such as cracks in the plugs, can also occur.

With continuing reference to FIG. 3, a fourth type of defect, denoted by DEF4 is internal to honeycomb structure 12 and is where a portion of a wall 14 collapses into channel 20. This collapse can be total as shown, or it can be partial. A similar type of defect, denoted by DEF5, is also internal to honeycomb structure 12 and occurs when extra material resides in a channel 20 in a manner that either partially or completely obstructs the channel. While defects DEF4 and DEF5 may not result in filter leaks, they can reduce the flow through the filter and reduce filter performance. Note that defects DEF4 and DEF5 can form in an unplugged honeycomb structure 12 as well as in a plugged honeycomb structure, and are shown in a plugged honeycomb structure for ease of illustration. These type of defects are called "material" defects in order to distinguish them from "plug" defects associated with plugs 30.

Another type of material defect is denoted by DEF6 and is where there is an opening (e.g., a crack or a hole) formed in wall 14. Hole-type material defect DEF6 may be sufficiently large to transmit a detectable amount of light to the adjacent channel, which also results in a reduction in the intensity of light traveling down the channel, as discussed in greater detail below.

General Optics-Based Defect Detection System

Figure 4:
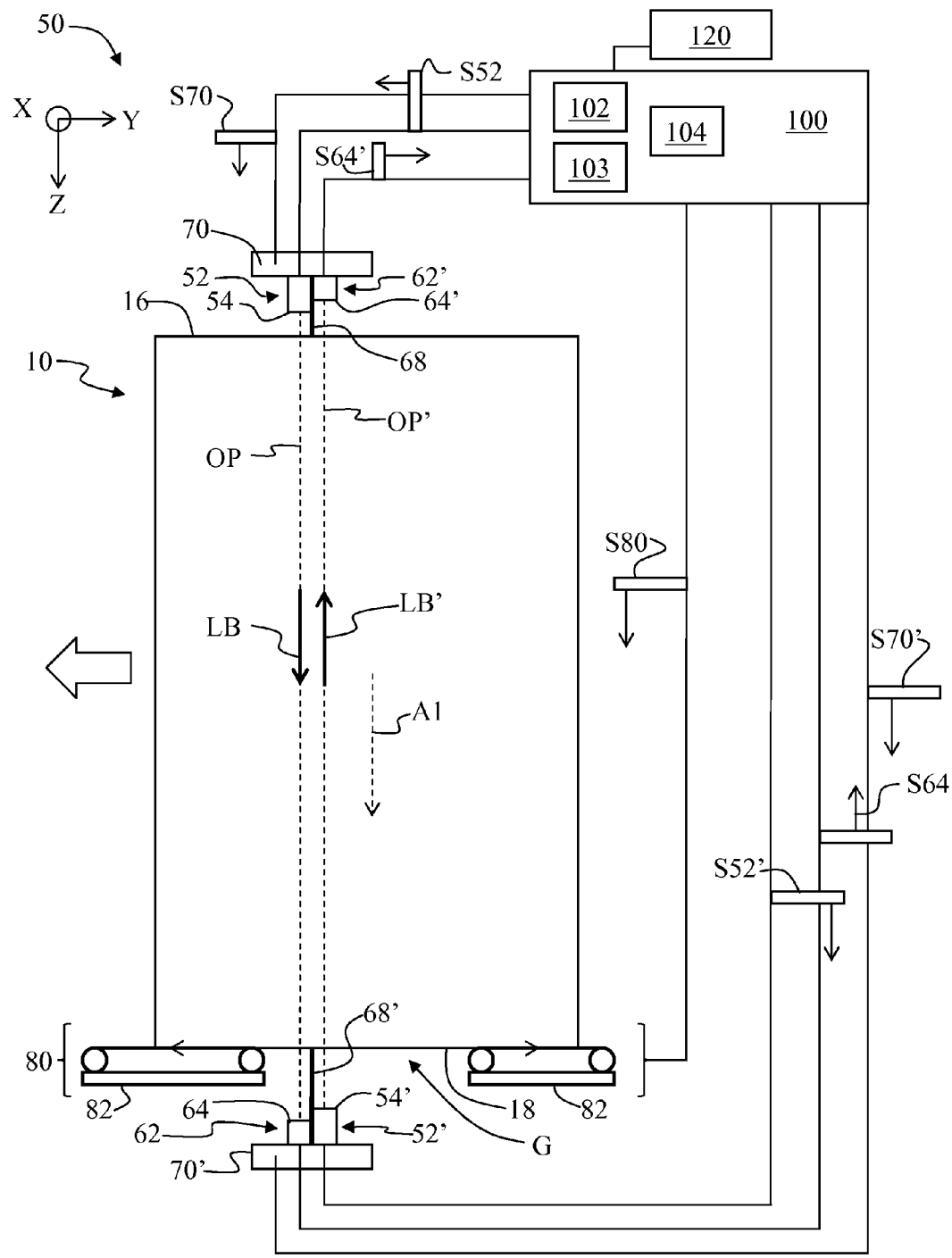
FIG. 4 is a schematic diagram of a generalized embodiment of an optics-based defect detection system according to the present invention with a ceramic filter body operably arranged therein.

FIG. 4 is a schematic diagram of a generalized embodiment of an optics-based defect detection system ("system") 50 according to the present invention with a ceramic filter body 10 operably arranged therein. System 50 includes a light source unit 52 arranged adjacent end 16, and an associated detector unit 62 arranged adjacent end 18. Light source unit 52 includes at least one light source element 54, and detector unit 62 includes at least one detector element 64. Light source unit 52 and detector unit 62 are aligned in the Z-direction along an optical path OP' so that the at least one light source element 54 is aligned with the at least one detector element 64. Light source unit 52 and detector unit 62 are in optical communication through at least one channel 20 in the absence of either defect-free plugs 30 or light-blocking channel defects DEF, such as those described above.

Example types of light source unit 52 and detector unit 62 are described in greater detail below. Generally, light source unit 52 can be a "single" or "point" light source that emits light over a small area (e.g., the area of a single channel end 22), a linear light source that emits a line of light (e.g., across ceramic filter body end 16), or a two-dimensional light source that blanket illuminates the entire ceramic filter body end 16. Similarly, detector unit 62 can be a "single detector" that detects light over a small area (e.g., the area of a single channel end 24), a linear detector that detects light along a line, or a two-dimensional detector that detects light over the entire ceramic filter body end 18.

With continuing reference to FIG. 4, in an example embodiment, a second light source unit 52' is arranged adjacent end 18 and a second detector unit 62' is arranged adjacent end 16 so as to be in optical communication through at least one channel 20 in the absence of defect-free plugs 30 or light-blocking material defects DEF within the at least one channel. Light that travels from one channel end to the other is usually divergent, so that light passing through a defect will also generally be divergent. Consequently, arranging detector units 62 and 62' as close as possible to ceramic filter body ends 16 and 18 in a "double-ended" arrangement for system 50 allows for detecting light as close as possible to plugs 30. In a single-ended embodiment of system 50, illuminating a plug 30 that resides at the light-source end means that any light transmitted through the plug needs to travel substantially the entire length of ceramic filter body 12 before being detected. Because this light will diverge and diffuse as it travels down channel 20, it will be attenuated and become difficult to detect.

In an example embodiment, detector units 62 and 62' are arranged such that their respective detector elements 64 and 64' are at a distance from 1 mm to 10 mm from their respective ceramic body ends 18 and 16.

Having two light source units 52 and 52' and two detector units 62 and 62' as configured in the double-ended system 50 of FIG. 4 allows for close-up light detection without having to adjust ceramic filter body 10. With a single-ended system 50 having only one light source unit 52 and one detector unit 62, ceramic filter body 10 would need to be rotated by 180° about the Y-axis and then re-measured to achieve close-up light detection at both ceramic filter body ends 16 and 18. Having to flip ceramic filter body 10 to perform a second close-up measurement adds time, complexity and cost to the defect detection process. The remainder of the discussion of the general embodiment of system 50 thus focuses mainly on dual light-sources/dual detectors or "double ended" embodiments.

In an example embodiment, light source unit 52 and detector unit 62' are supported by a first X-Y-Z stage 70 adjacent ceramic filter body end 16, while light source unit 52' and detector unit 62 are supported by a second such stage 70' adjacent opposite ceramic filter body end 18. This allows for the two light source units and the two detector units to move synchronously and to maintain a fixed position relative to ceramic filter body 10 and to each other. Movability in the Z-direction for each stage 70 and 70' also allows for close placement of light source units 52 and 52' and detector units 62 and 62' relative to ceramic filter body ends 16 and 18. Stages 70 and 70' preferably are also independently adjustable to facilitate coarse and/or fine alignment.

In an example embodiment, a first light shield 68 is placed between light source unit 52 and detector unit 62', and a second light shield 68' is placed between light source unit 52' and detector unit 62. This arrangement ensures that only light from light source unit 52 is detected by detector unit 62 and that only light from light source unit 52' is detected by detector unit 62'.

In an example embodiment, ceramic filter body 10 is supported and carried by a conveyor system 80 configured to move the ceramic filter body past the light source units 52 and 52' and detector units 62 and 62'. In an example embodiment, conveyor system 80 includes a stage 82 for positioning ceramic filter body 10 in the X-Y plane and optionally positioning the ceramic filter body along the Z-direction. Conveyor system 80 includes a gap G through which detector unit 62 and light source unit 52' can optically communicate with their light source unit and detector unit counterparts (52 and 62', respectively). In another example embodiment, system 50 is configured so that ceramic filter body 10 is arranged on its side, i.e., with its central axis A1 in the Y-direction.

System 50 includes a controller 100 operably (e.g., electrically) connected to light source units 52 and 52', to detector units 62 and 62', to stages 70 and 70', and to conveyor system 80. Controller 100 is configured to control the operation of these system components to effectuate the operation of system 50 as a whole. In an example embodiment, controller 100 includes a processor 102 (e.g., a digital processor) and a memory unit 104 operably connected to the processor and that serves as a computer-readable medium capable of storing instructions for instructing the controller to carry out the various methods of the present invention as described in greater detail below. In an example embodiment, controller 100 includes an analog-to-digital (A/D) converter 103 that receives analog detector signals S64 and converts them to digital detector signals for processing by (digital) processor 102.

In an example embodiment, controller 100 comprises a programmable computer capable of performing digital logic operations, digital control operations, and/or image processing. In an example embodiment, system 50 includes a display unit 120 operably connected to controller 100 and configured to display graphical and/or visual representations of data collected and processed by the controller.

General Method of Operation

For the sake of illustration, it is assumed here once again that system 50 is a double-ended system. Embodiments with a single light source unit 52 and a single detector unit 62 work in an analogous fashion, with some differences, as discussed below.

In the operation of system 50, light source units 52 and 52' are aligned with their associated detector units 62 and 62', and positioned at select locations relative to ceramic filter body 10. To facilitate the alignment and positioning operations to establish optical communication, in an example embodiment, ceramic filter body 10 is removed from system 50, and the alignment of light source unit 52 with detector unit 62 and the alignment of light source unit 52' with detector unit 62' is carried out by activating the light source units and taking readings at the associated detector units.

Light source units 52 and 52' are activated via respective control signals S52 and S52' sent from controller 100. These control signals S52 and S52' causes respective light source units 52 and 52' to generate respective light beams LB and LB' that enter the respective open channel ends 22 and 24 and proceed down each channel 20 when ceramic filter body 10 is operably arranged in system 50. However, when ceramic filter body 10 is removed, light beams LB and LB' are in direct optical communication with detector units 62 and 62'.

In response to detecting light, detector elements 64 and 64' of respective detector units 62 and 62' generate respective electrical detector signals S64 and S64', which are conducted to controller 100. Detector signals S64 and S64' are used to establish alignment (e.g., by adjusting the light source units 52 and 52' and the detector units 62 and 62' to maximize the detector electrical signals) and to provide detector base-line readings.

Once the alignment of light source units 52 and 52' with their corresponding detector units 62 and 62' is carried out and optical communication established, ceramic filter body 10 is placed into system 50 and moved into position in between light source units 52 and 52' and detector units 62 and 62'. Prior to initiating the defect detection measurement method, stages 70 and 70' can also be used to adjust the position of light source units 52 and 52' and detector units 62 and 62' relative to one another as well as to ceramic filter body 10.

The movement of stages 70 and 70' is controlled by respective control signals S70 and S70' from controller 100. Conveyor system 80 is controlled by a conveyor control signal S80 from controller 100 and can be used to move ceramic filter body 10 in and out of system 50 as needed, as well as to position the ceramic filter body within the system in the X-Y plane as well as in the Z-direction. Controller 100 tracks the movement of stages 70 and 70' and conveyor system 80 so that the position of ceramic filter body 10 relative to light source units 52 and 52' and detector units 62 and 62' is known.

It is worth noting here that for most ceramic bodies 10, channels 20 are packed relatively close together. For example, a honeycomb structure 12 having 625 channels per square inch has 25 channels per linear inch, which translates into a center-to-center spacing (i.e, a channel width $W_C$) of about 0.04 inches or about 1 mm. This makes it impractical to place light source unit 52 and detector unit 62' so close together so as to be aligned with adjacent channels 20. Thus, light source unit 52 and detector unit 62' are preferably spaced apart far enough to prevent "cross talk" therebetween. In an example embodiment, spacing between adjacent light source and detector units 52 and 62' (as well as between adjacent light source and detector units 52' and 62) is between 5 mm to 15 mm. The exact spacing depends on the size of light source unit 52 and detector unit 62' and the angular spread of light beams LB and LB'.

Figure 5A:
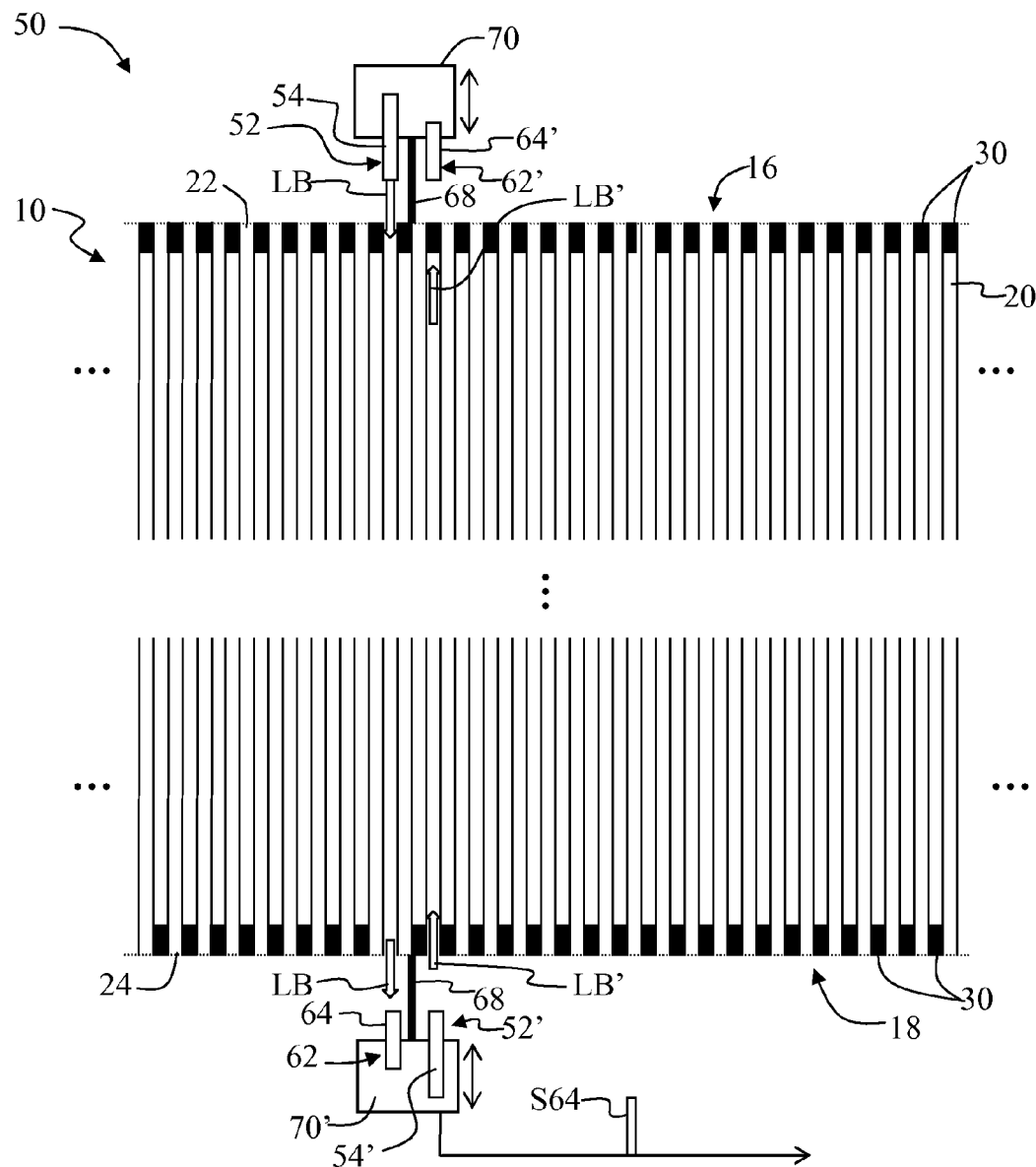
FIG. 5A is a close-up view of a portion of the system of FIG. 4 and shows the details of the ceramic filter body ends, the plugs alternately formed therein, as well as a plug defect that allow light to pass through to a detector unit.

FIG. 5A is a close-up view of a portion of system 50 as shown in FIG. 4 and shows the details of ceramic filter body ends 16 and 18 with plugs 30 formed in alternating ends 22 and 24 of channels 20. Light source unit 52 is aligned with one or more open channel ends 22 at ceramic filter body end 16, while its associated detector unit 62 is aligned with the corresponding one or more plugged channel ends 24 at ceramic filter body end 18. Likewise, light source unit 52' is aligned with one or more open channel ends 24 at ceramic filter body end 18, while its associated detector unit 62' is aligned with the corresponding one or more plugged channel ends 22 at ceramic filter body end 16.

With reference to FIG. 4 and FIG. 5A, once light source units 52 and 52' and the associated detector units 62 and 62' are properly aligned with each other and are at respective desired locations relative to ceramic filter body 10, controller 100 initiates the operation of the light source units via respective control signals S56 and S56'. This causes light source units 52 and 52' to once again generate respective light beams LB and LB' that now enter the respective open channel ends 22 and 24 and proceed down each channel in opposite directions (i.e., the +Z and −Z directions, respectively). In the case where each select channel end 22 and 24 is properly plugged, no light from light beam LB or LB' exits ceramic filter body 10 through the corresponding plug 30. Thus, no light is detected by any of the one or more detector element(s) 64 or 64' in respective detector units 62 and 62'.

In the case where one of plugs 30 is defective so that a perfect seal is not formed, a detectable portion of light from the corresponding light beam will pass through the plug. For example, with continuing reference to FIG. 5A, consider the channel 20 that is aligned with light source unit 52 and detector unit 62 where there is no plug at either channel end 22 or 24 of the channel through which light beam LB travels. In this case, the one or more detector elements 64 adjacent end 24 of the corresponding channel 20 will detect a relatively large amount of light from light beam LB. The one or more detector elements 64 will then generate respective one or more detector electrical signals S64 that are representative of the amount of light detected. Note that in FIG. 5A, light beam LB' from light source unit 52' is blocked by a "good" plug 30 at channel end 22 immediately adjacent channel 20 through which the light beam travels. Accordingly, no light is detected by detector unit 62'.

The position of the one or more detector element 64 provides information about the location of the plug defect—in this case, the X-Y location of channel end 24 where plug 30 is missing. This location detection ability is further enhanced by providing multiple detector elements 64 per channel width $W_C$, as discussed in greater detail below. Defect location information is important because, in an example embodiment, it is used to direct a robotic tool (not shown) to fix certain types of defects, and in particular missing plugs 30.

Figure 5B:
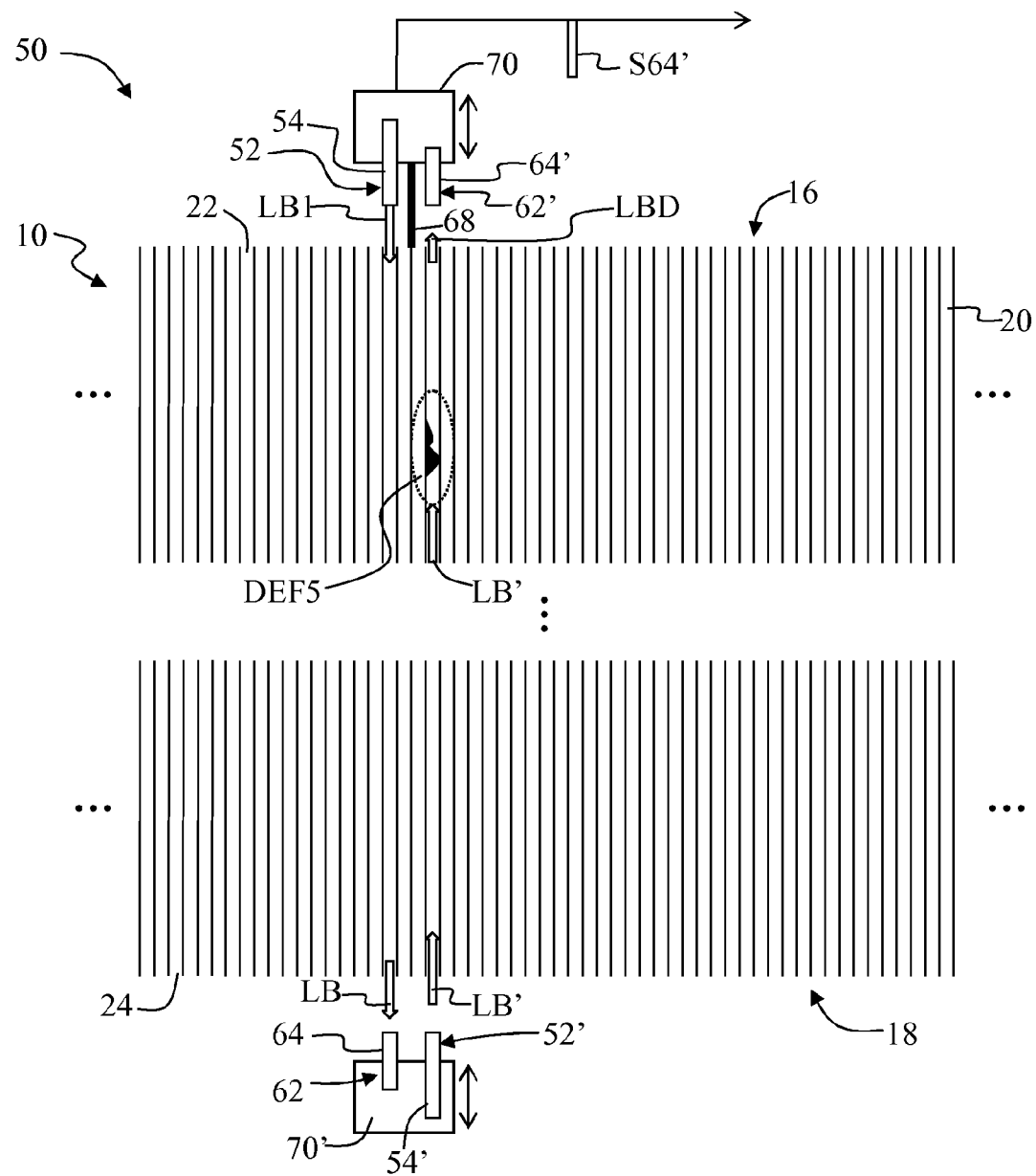
FIG. 5B is similar to FIG. 5A and illustrates an example embodiment wherein the defect detection system is used to measure a ceramic filter body having unplugged ends to detect material defects internal to the honeycomb structure.

FIG. 5B is similar to FIG. 5A, and illustrates an example embodiment wherein system 50 is used to measure a ceramic filter body 10 having unplugged channel ends 22 and 24 so that the system can detect defects, such as defect DEF5 (FIG. 3) within honeycomb structure 12. The operation of system 50 as applied to an unplugged ceramic filter body 10 is similar to that for a plugged ceramic filter body in that obstructions or other defects within channels 20 either entirely block or reduce the amount of light that reaches detector units 62 and 62' as compared to the case wherein light beams LB and LB' travel down unobstructed channels 20.

In the case where a detectable portion (intensity) of light LBD' from light beam LB' makes it past material defect DEF5, this light portion is detected by detector unit 62' and detector electrical signal S64', which corresponds to the amount of light detected, is communicated to controller 100. In an example embodiment, a honeycomb structure 12 intended to be plugged is measured in its unplugged state to determine if there are internal material defects, such as defects DEF4-DEF6, prior to being plugged. This is because certain types of material defects, such as defects DEF4 and DEF5, can block one or more channels 20 and create the appearance of one or more defect-free plugs 30. In an example embodiment, the method of detecting material defects includes processing the first or first and second electrical detector signals S64. or S64 and S64', to detect a reduction in the intensity in at least one of the first and second light beams LB and LB' as compared to the light intensities of these beams traveling through defect-free channel 20. Once the material defects are characterized, or once it is determined that there are essentially no such defects, then the measured honeycomb structure 12 can then be plugged and then tested for plug defects.

Variations in the amounts of light detected by detector units 62 and 62' serve to indentify the channel location of the defects. The use of multiple detector elements 64 and 64' per channel width $W_C$ for detector units 62 and 62' provide the ability to resolve variations in the intensity of light exiting the channel ends 22 and 24. Such variations provide insight into the type and location of the defect present in the particular channel 20.

Once all of the channels 20 of the plugged or unplugged ceramic filter body 10 are subject to the above-described measurement process, the detector electrical signals S64 and S64' collected by controller 100 in memory unit 104 are processed by processor 102. In an example embodiment, the processed data is displayed on display 120.

Figure 6A:
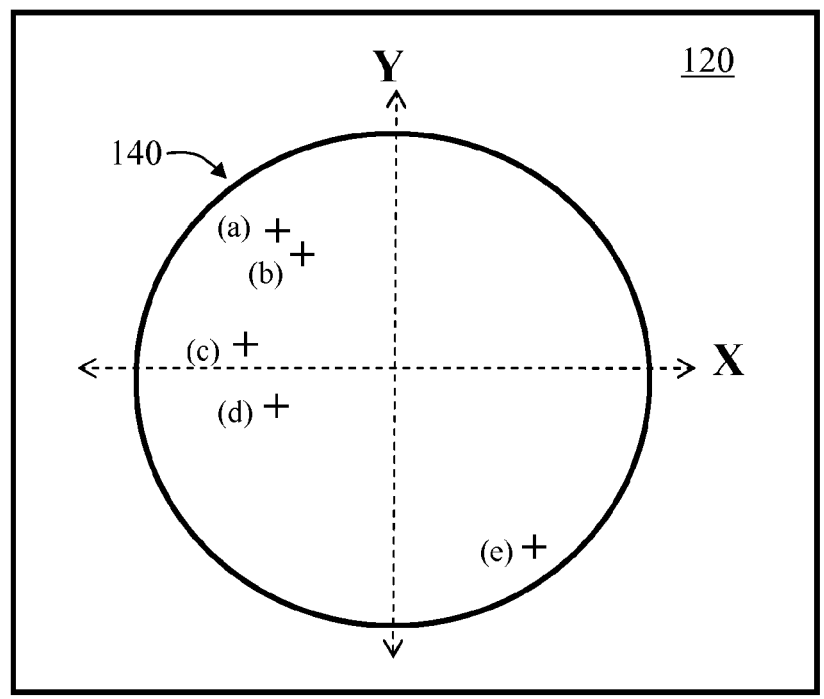
FIG. 6A is an example embodiment of an end image of the ceramic filter body as generated by a controller and displayed on a display, showing locations where light is detected by the detector unit.

FIG. 6A is an example embodiment of an end image 140 of the measured ceramic filter body 10 as formed from the data provided by detector signals S64 and processed by controller 100. The end image shows locations (a) through (e) where light was detected by detector unit 62. This information can be used to inspect ceramic filter body 10 more closely at the select locations and/or to direct a robot to fix the defects. The same type of end image 140 can also be displayed for data provided by detector signals S64' so that data taken at both ends 16 and 18 of ceramic filter body 10 can be viewed simultaneously.

Figure 6B:
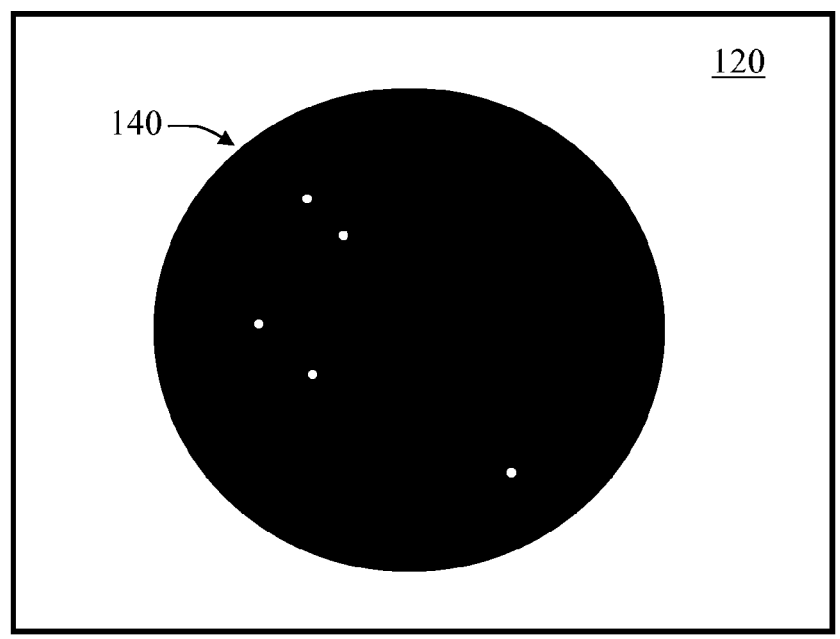
FIG. 6B is similar to FIG. 6A, but illustrates a "dark field" embodiment of the end image where detected light shows up as white spots in a dark background.

FIG. 6B is similar to FIG. 6A, but illustrates a "dark field" embodiment of end image 140 that is more representative of what detector unit 62 actually "sees" when the entire ceramic filter body 10 is measured. FIG. 6B shows the locations where light is detected as white spots on a dark background.

Because controller 100 controls the position of light source units 52 and 52' and detector units 62 and 62' relative to ceramic filter body 10, the precise positions of detected defects are tracked and stored in memory unit 104 and optionally displayed on display 120 or otherwise communicated to a system user.

To summarize, an example method of operation involves detecting defects in a ceramic filter body 10 by positioning a first light source unit 52 having at least one first light source element 54, and a first detector unit 62 having at least one first detector element 64 to be adjacent the first and second ends ceramic filter body ends 16 and 18, respectively, so that the at least one first light source element and the at least one first detector element are capable of being in optical communication through a corresponding at least one first channel 20. Here, the phrase "capable of" is used because either defect-free plugs 30 or material defects (e.g., DEF4 and DEF5) within honeycomb structure 12 may block light beam LB and thus cut off the optical communication.

The method further includes transmitting at least one first light beam LB from the first light source unit 52 to the first detector unit 62 through the at least one first channel 20, and detecting first light (e.g., a detectable light portion LBD) from the at least one first light beam with the at least one first detector element 64 and, in response thereto, generating at least one first electrical detector signal S64 representative of the detected first light.

The method also includes processing the at least one first electrical detector signal to determine if at least one first defect exists within the at least one first channel. The "double-ended" version of the method includes performing the same operation as described above, but with a second light source unit 52' and a second detector unit 62' through at least one second channel 20 (i.e., different than the first channel 20) to determine if at least one second defect exist within the at least one second channel.

In the case where the ceramic filter body 10 is unplugged, detector signals S64 and S64' are used in the double-ended embodiment of system 50 to determine whether there is a reduction in the intensity of one or both light beams LB and LB' from their baseline or "defect-free" channel intensity. The reduction in intensity in one or both light beams LB and LB' is representative of the presence of at least one "first" defect and at least one "second" defect within one or both of the at least one first channel and the at least one second channel, respectively.

FIRST EXAMPLE EMBODIMENT

Figure 7:
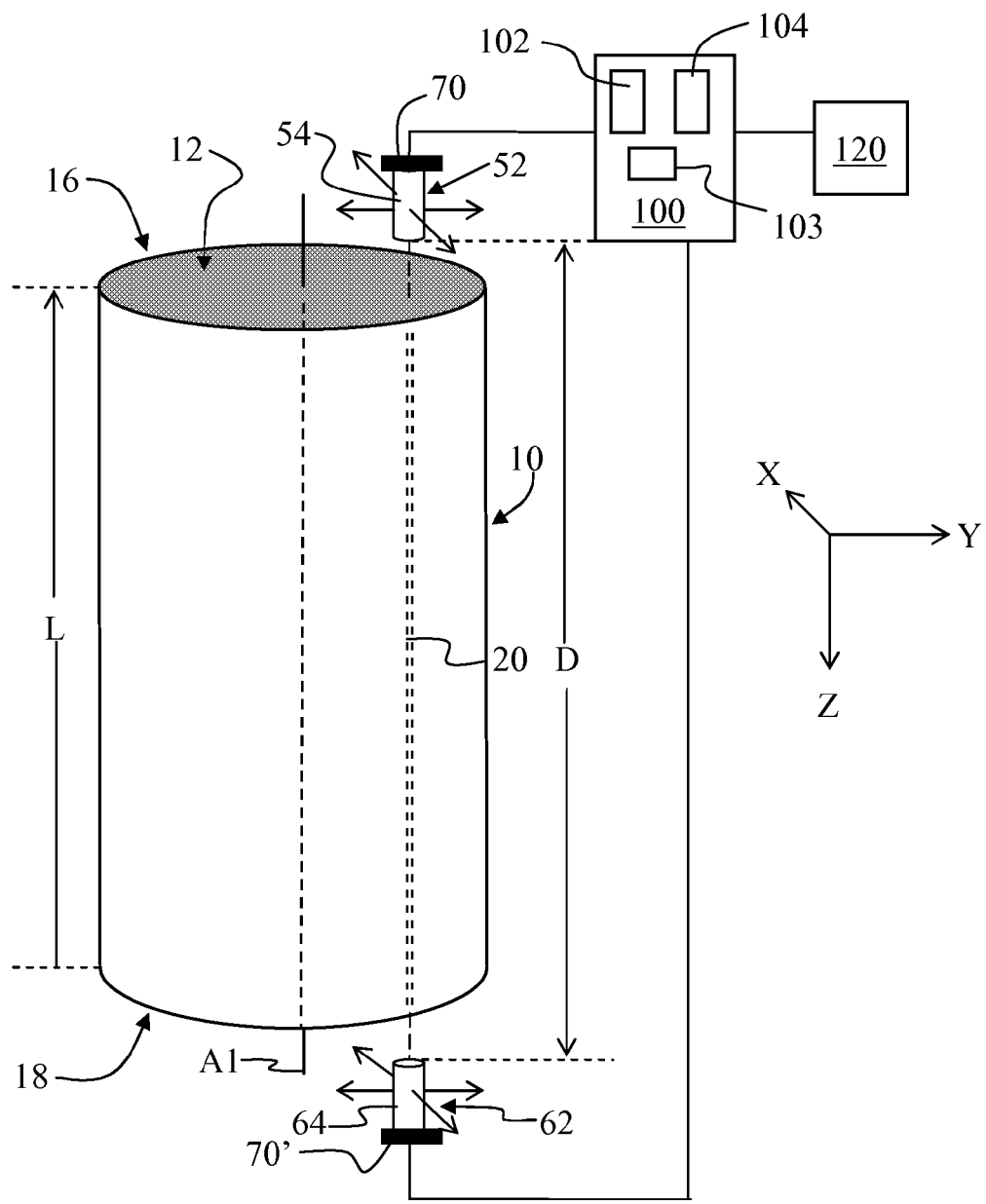
FIG. 7 illustrates an example embodiment of a "single-ended" version of the defect detection system of the present invention, wherein a light source unit has a single light source element and the detector unit has a single detector element.

FIG. 7 illustrates an example embodiment wherein light source unit 52 has a single light source element 54 and detector unit 62 has a single detector element 64. In an example embodiment, light source element 64 has a width on the order of the size of channel width $W_C$. In an example embodiment, channel width $W_C$ ranges from about 2.5 mm to about 0.025 mm.

In an example embodiment, light source element 64 comprises a light-emitting photodiode that has a size (i.e., active area) of, for example, 1 mm$^2$ or smaller. In another example embodiment illustrated in FIG. 8A and FIG. 8B, light source unit 52 comprises an optical fiber 200 that has, for example, a core 202 and a surrounding cladding 204, with the core having a diameter anywhere from about ten microns (for a single-mode fiber) to several hundred microns for a multi-mode fiber. Optical fiber 200 has an input end 210 and an output end 212. Light source unit 52 includes a light source 220 such as an LED or a laser. Light source 220 is optically coupled to optical fiber input end 210, e.g., via a lens 230. Optical fiber output end 212 then serves as an effective light source element 54 having a relatively small "active area" (i.e., substantially that of core 202) that emits a divergent light beam LB.

Figure 8A:
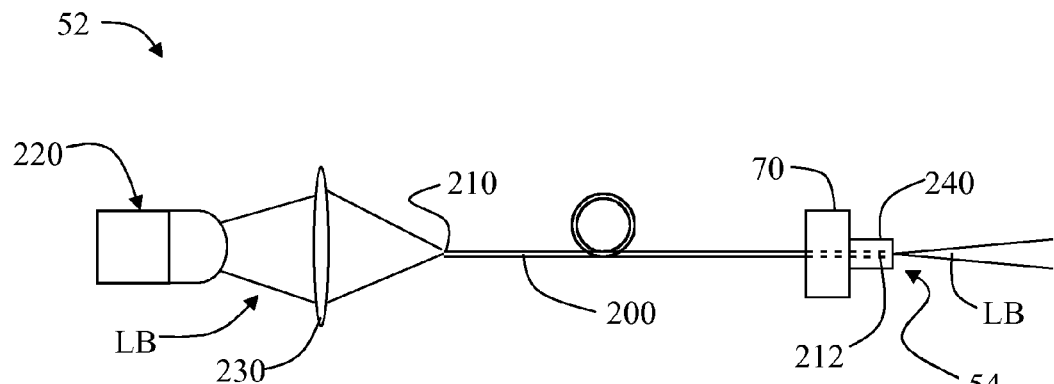
FIG. 8A is a schematic side view of an example embodiment of a light source unit suitable for use in the system of FIG. 7 and that includes an optical fiber to create a small-area light source element.
Figure 8B:
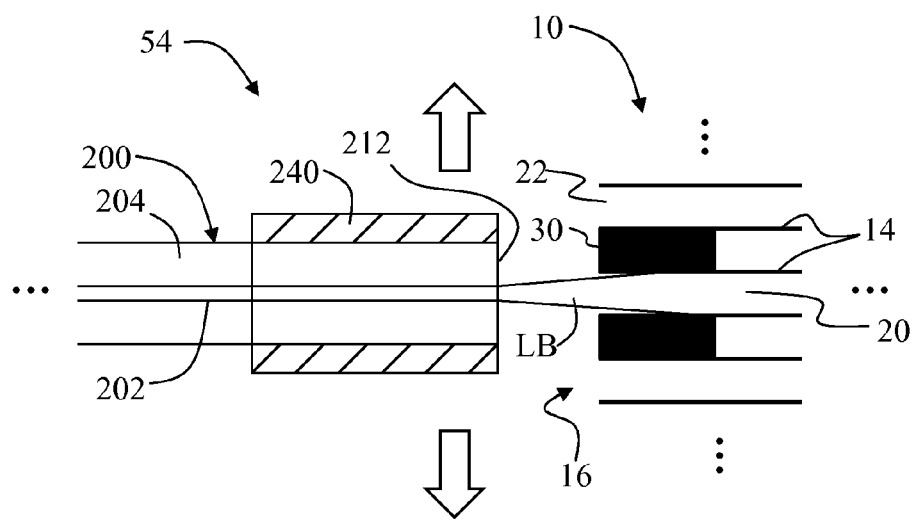
FIG. 8B is a close-up side view of the light source unit of FIG. 8A and shows an end portion of the ceramic filter body end and how a divergent light beam from the fiber end enters the open channel end.

In an example embodiment shown in the close-up view of FIG. 8B, a portion of optical fiber 200 at output end 212 is held within a connector 240 to facilitate supporting and moving the optical fiber output end into position relative to ceramic filter body 10 and channels 20 therein. In an example embodiment, connector 240 is supported by stage 70, as shown in FIG. 8A.

The embodiment of system 50 of FIG. 7 requires coordinated movement of light source unit 52 and detector unit 62. Note that a double-ended version of this example embodiment of system 50 can be formed using two light source units 52 and 52' each having a single light source element, and two detector units 62 and 62' each having a single detector element. Because the single-ended and double-ended versions of the present example embodiment of system 50 are relatively complex and time-consuming to operate, it is best suited for special inspection situations, e.g., when single-channel inspections are needed or when select regions of ceramic filter body 10 need to be very accurately inspected.

SECOND EXAMPLE EMBODIMENT

Figure 9:
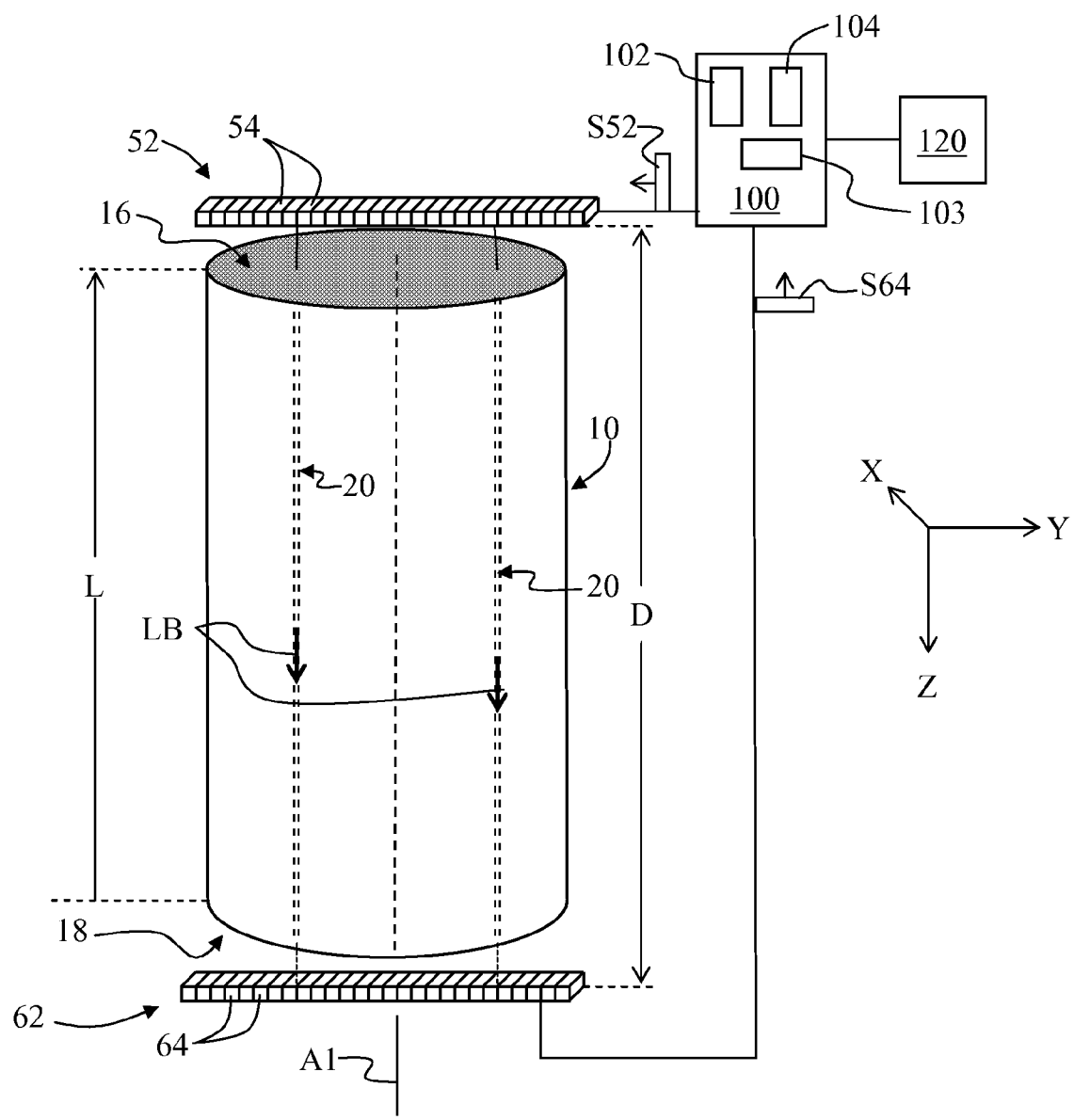
FIG. 9 is a schematic diagram similar to FIG. 7 and illustrates an example embodiment of a "single-ended" version of the defect detection system of the present invention that includes a linear light source unit and a linear detector unit.

FIG. 9 is a schematic diagram similar to FIG. 7 and illustrates an example embodiment of a "single-ended" version of system 50 that employs a "linear" light source unit 52 having a linear array of light source elements 54 and a "linear" detector unit 62 having a linear array of detector elements 64. In an example embodiment, linear detector 62 comprises a sensor array having detector elements 64 with a density in the range from 200 to 2,400 "dots per inch" (dpi), which corresponds to a detector element ("pixel") size in the range from about 125 µm to about 10 µm. In an example embodiment, detector unit 62 comprises at least one contact image sensor, such as the type used in scanners, copiers and fax machines. In an example embodiment, multiple contact sensor units can be arranged end-to-end to form a long linear detector unit 62.

For detector elements 64 on the order of 125 µm across or smaller, multiple detector elements can be used to detect light that exits at a given channel end 24 (not shown in FIG. 9; see FIG. 5B). In an example embodiment, there is a number N1 of detector elements 64 per channel width $W_C$, and in a particular example embodiment, $2 \leq N1 \leq 25$. This allows for detector unit 62 to resolve and locate small defects in ceramic filter body 10.

In an example embodiment, linear light source unit 52 and linear detector unit 62 are scanned over respective ends 16 and 18 of ceramic filter body 10. In another example embodiment, ceramic filter body 10 is conveyed past linear light source unit 52 and linear detector unit 62 using conveyor system 80. In an example embodiment, two linear light source units 52 and 52' and two linear detector units 62 and 62' are used to form a "double-ended" system 50 as shown in FIG. 4. In an example embodiment, the time it takes to scan the entire ceramic filter body 10 and obtain data from both ceramic filter body ends 16 and 18 is about five seconds.

In one example scanning embodiment, linear light source unit 52 remains stationary to illuminate a select row of channels 20 while linear detector unit 62 scans over the corresponding channel ends 24. The linear light source unit 52 is then moved to the next row of channels 20 and the linear detector unit 62 scans the next corresponding channel ends 24. This "step and scan" process is repeated until all of channels 20 of ceramic filter body 10 are inspected. This process can be modified by pulsing or modulating light source unit 52 as the linear detector unit 62 continuously moves, with the timing of the pulsing or modulating such that the detector elements 64 move by a detector element width ("pixel width") in the scan direction for each light pulse.

In another example embodiment, linear detector unit 62 includes enough rows of detector elements to cover the entire width $W_C$ of a channel 20 in both the X and Y directions. In the context of the present invention, this particular arrangement for detector unit 62 is considered a "linear detector" because such a detector unit detects or covers one row or "line" of channels 20 at a time.

FIG. 10A is a close-up view of a single ceramic filter body channel 20, showing light beam LB traveling in the channel and the light being blocked by a defect-free plug 30. Since there is no defect in plug 30, no substantial portion of light beam LB inputted at channel end 22 at ceramic filter body end 16 reaches any of detector elements 64, so no detector signal S64 is generated. Alternately, a baseline detector signal S64 (shown in dashed-line format) is generated that represents "zero" light detected.

FIG. 10B shows a channel end image 138 formed by controller 100 for the particular set of detector elements 64 that are positioned to detect light that passes through the particular channel end 24. Since no light is detected, channel end-image 138 is black. Note that in FIG. 10A, there are four detector elements 64 per channel width $W_C$, for a total of 16 detector elements 64 per channel end 24.

FIG. 11A is similar to FIG. 10A, but shows a defect DEF2 in plug 30 that allows a detectable light portion LBD from light beam LB to pass through. Detectable light portion LBD is detected by a subset of detector elements 64 that are positioned to detect light that passes through the particular channel end 24. This leads to a corresponding detector signal S64 being generated that contains information about detectable light portion LBD.

FIG. 11B is similar to FIG. 10B and shows the gray scale channel end image 138 formed by controller 100 that indicates the relative location and size of defect DEF2 in plug 30 based on detected light portion LBD as gray scale portions 139A through 139D that correspond to individual detector elements 64 activated by light portion LBD.

For the case where ceramic filter body 10 is unplugged, the farther away an internal material defect is from detector unit 62, the more diffuse the detectable light portion LBD from light beam LB will tend to be when it finally reaches the detector unit. Thus, some material defects will cause an overall reduction in the intensity of light beam LB so that multiple detector elements 64 for a given channel 20 will each detect about the same light intensity. For material defects that fall closer to the detector unit 62, the intensity variations will generally be sharper because the light has less distance over which to diverge and diffuse. Thus, information gleaned from the overall intensity reduction and the variations in intensity associated with a given channel 20 provide insight as to the location and type of material defects in ceramic filter body 10.

Figure 12A:
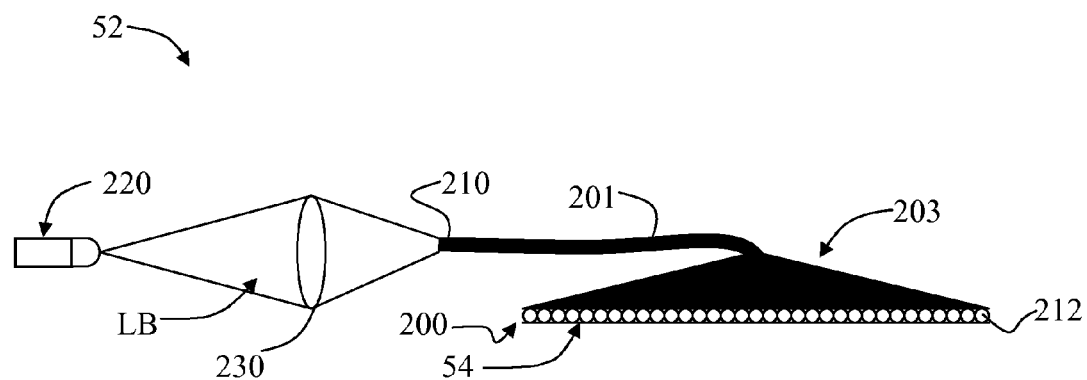
FIG. 12A is a schematic diagram of an example embodiment of a linear light source unit formed using multiple optical fibers in a fiber optic cable that includes a fan-out section.

Linear light source unit 52 can have a number of different forms. FIG. 12A is a schematic diagram of a first example embodiment of linear light source unit 52 similar to that shown in FIG. 8A, except that a plurality of optical fibers 200 are carried in a fiber optic cable 201. Cable 201 is coupled to light source 220 at one end, and includes a fan-out section 203 configured so that fiber ends 212 serve as a line of light source elements 54.

Figure 12B:
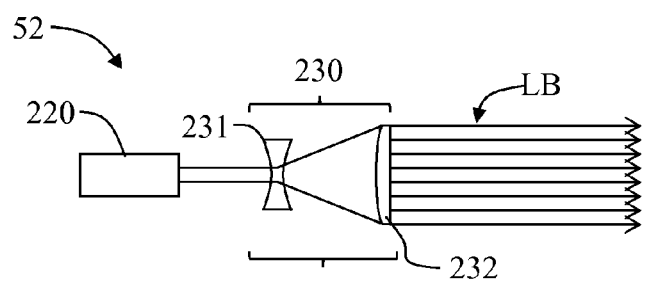
FIG. 12B is a schematic diagram of an example embodiment of a linear light source unit that uses cylindrical divergent and convergent lenses to form a collimated line source from a laser beam.

FIG. 12B is a schematic diagram of another example embodiment of light source unit 52 where light source 220 is a laser, and lens 230 is includes cylindrical diverging lens 231 and a cylindrical converging lens 232 that forms a collimated-line light beam LB.

Figure 12C:
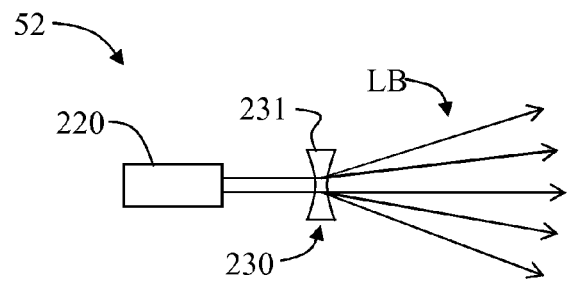
FIG. 12C shows a light source unit similar to that of FIG. 12B, but that uses only the cylindrical divergent lens to form a divergent line source.

FIG. 12C is a schematic diagram of another example embodiment of light source unit 52 similar to FIG. 12B and illustrates an example embodiment where only cylindrical diverging lens 231 is used in lens 230 to form a diverging line type light beam LB.

Figure 13:
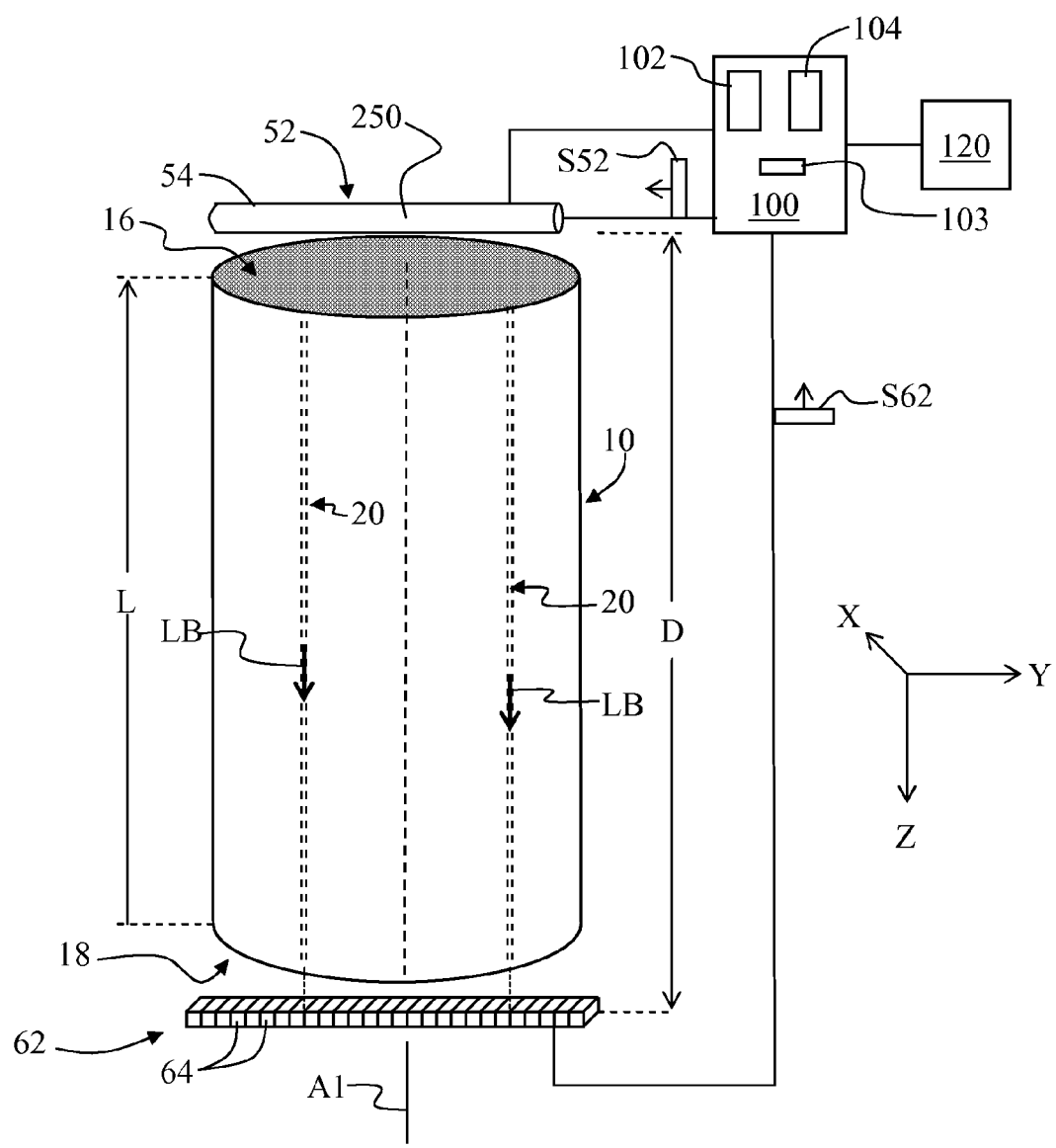
FIG. 13 is a schematic diagram similar to FIG. 9 and illustrates an example embodiment of a defect detection system where the light source unit includes a tubular fluorescent bulb as an extended light source element.

FIG. 13 is a schematic diagram similar to FIG. 10, but illustrates an example embodiment wherein linear light source unit 52 includes an extended light source element 54 in the form of a fluorescent light tube 250. In an example embodiment, fluorescent light tube 250 is a fluorescent aperture lamp, which includes an elongated aperture through which a relatively large amount of light is emitted. Fluorescent light tube 250 allows for easily illuminating a large line portion of ceramic filter body end 16, while linear detector unit 62 limits the detection of light to a select line (row) of channels 20. The divergent illumination provided by fluorescent light tube 250 also allows for greater tolerance to channel alignment offsets that can occur in honeycomb structure 12.

THIRD EXAMPLE EMBODIMENT

Figure 14:
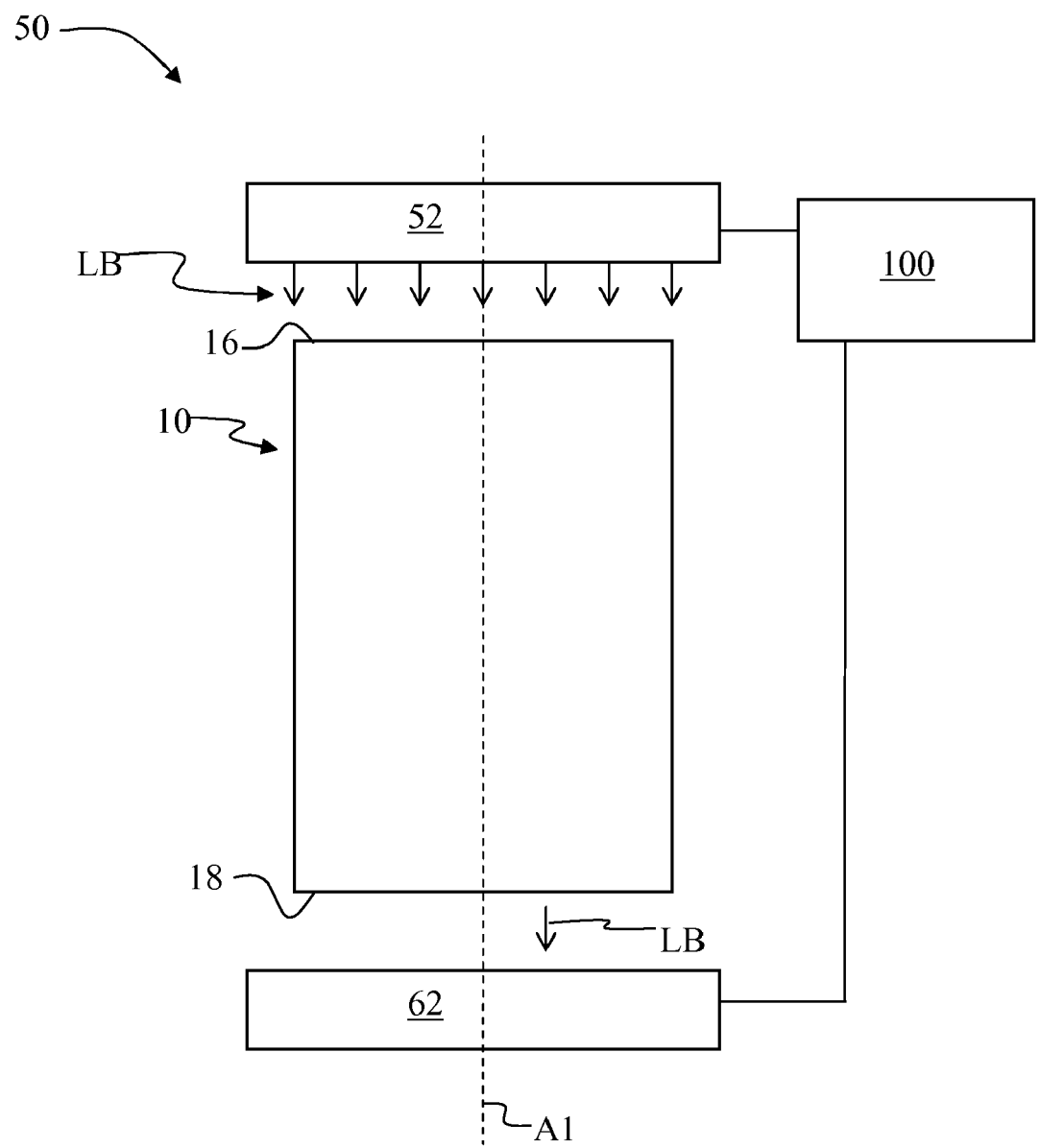
FIG. 14 is a schematic side view of an example embodiment of a detect detection system that uses a two-dimensional light source unit and a two-dimensional detector unit to illuminate the entire end of the ceramic filter body and to detect light over the entire opposite end of the ceramic filter body.

FIG. 14 is a schematic diagram of an example embodiment of system 50 similar to that of FIG. 10, but wherein light source unit 52 is configured to illuminate the entire or substantially the entire end 16 of ceramic filter body 10, and detector unit 62 is configured to detect light exiting over the entire end 18 of the ceramic filter body. In this example embodiment, light source unit 52 comprises, for example, an array of fluorescent light tubes, or an array of LEDs.

Detector unit 62 comprises, for example, an array of linear detectors, e.g., an array of contact image sensors, to form a 2-D detector array that covers the entire or substantially the entire ceramic filter body end 18. Alternatively, detector unit 62 can comprise an array of smaller 2-D detectors to form a larger 2-D detector unit.

Because ceramic bodies 10 can have diameters about 3" to 17" (i.e., about 7.6 cm to about 43.2 cm), it is relatively expensive to form a 2-D detector unit and a 2-D light source unit that cover the entire or substantially the entire ceramic filter body diameter. Also, covering the entire ceramic filter body end 16 with light source unit 52 and the entire ceramic filter body end 18 with detector unit 62 prevents the detection of light in close proximity to both ends of ceramic filter body 10 at once and essentially precludes forming an affordable and non-complex version of the desirable "double ended" embodiment of system 50.

FOURTH EXAMPLE EMBODIMENT

As discussed above, walls 14 of honeycomb structure 12 may have a defect DEF6 (see FIG. 3) in the form of an opening (e.g., a crack or a hole sufficient) in size to pass a detectable portion LBD of light beam LB to the adjacent channel 20. This detectable light portion LBD can then be detected by detector elements 64 at the end 24 of the adjacent channel. Likewise, the transfer of a portion of light from light beam LB to an adjacent channel reduces the intensity of light beam LB. This same phenomenon can apply in the opposite direction with light source unit 52', detector unit 62' and detectable light portion LBD'. Thus, the generation of electronic detector signals S64 and/or S64' in an adjacent channel 20 from the original channel of light travel for light beam LB and/or LB', along with a reduction in the intensity of light beams LB and/or LB' (as deduced from the electronic signals associated with detector unit(s) of the original channel(s)), is indicative of a opening-type defect DEF6 in honeycomb structure 12.

It will be apparent to those skilled in the art that various modifications to the example embodiments of the invention as described herein can be made without departing from the spirit or scope of the invention as defined in the appended claims. Thus, it is intended that the present invention covers the modifications and variations of this invention provided they come within the scope of the appended claims and the equivalents thereto.

What is claimed is:

1. A method of detecting defects in a ceramic filter body having a honeycomb structure with first and second ends and an array of longitudinal channels between the first and second ends and having respective first and second channel ends, the method comprising:

positioning adjacent the honeycomb structure first end a first light source unit having multiple first light source elements that generate respective first light beams;

positioning immediately adjacent the honeycomb structure second end a first detector unit having multiple first detector elements per channel end for at least one first channel, so that the first light source and the first detector elements are capable of being in optical communication through the corresponding at least one first channel;

transmitting at least one of the first light beams from the first light source unit to the first detector unit through the at least one first channel;

detecting first light from the at least one of the first light beams with the multiple detector elements per channel and, in response thereto, generating at least one first electrical detector signal representative of a gray-scale variation in the detected first light for the at least one first channel; and processing the at least one first electrical detector signal to determine if at least one first defect exists within the at least one first channel.

2. The method of claim 1, further comprising for said processing:
calculating, for the at least one first defect, corresponding at least one defect position relative to the honeycomb structure second end based on the gray-scale variation in the first detected light for the at least one channel.

3. The method of claim 1, further comprising:
moving the ceramic filter body relative to the first light source unit and the first detector unit so as to detect the at least one first defect over substantially the entire ceramic filter body.

4. The method of claim 1, further comprising:
the multiple first detector elements each having a width of between about 10 microns and about 125 microns.

5. The method of claim 1, further comprising a number N1 of first detector elements per channel end, wherein $2 \leq N1 \leq 25$.

6. The method of claim 1, wherein the first light source elements are selected from the group of light source elements comprising: light-emitting diodes and lasers.

7. The method of claim 1, further comprising:
forming the first light source unit from multiple optical fibers.

8. The method of claim 1, wherein the ceramic filter body includes a plurality of first plugs arranged in select second channel ends adjacent the first detector unit, and wherein the at least one first channel is one of the select channels designated to include one of the first plugs, the method further comprising:
detecting first light that passes through either a) a defect in the first plug, or b) the at least one second channel end when the first plug is absent therefrom.

9. The method of claim 1, further comprising:
positioning adjacent the honeycomb structure second end a second light source unit having multiple second light source elements that generate respective second light beams;
positioning immediately adjacent the honeycomb channel first end a second detector unit having multiple second detector elements per channel end for at least one second channel, so that the second light source and the second multiple detector elements are capable of being in optical communication through the corresponding at least one second channel from the second to first channel ends;

transmitting at least one of the second light beams from the second light source unit to the second detector unit through the at least one second channel;

detecting second light from the at least one of the second light beams with the multiple detector elements per channel and, in response thereto, generating at least one second electrical detector signal representative of a gray-scale variation in the detected second light for the at least one second channel; and processing the at least one-second electrical detector signal to determine if at least one second defect exists within the at least one second channel.

10. The method of claim 9, wherein the ceramic filter body includes a plurality of first plugs arranged in select second channel ends adjacent the first detector unit, a plurality of second plugs arranged in select first channel ends adjacent the second detector unit, and wherein the at least one first and second channels are ones of the select channels designated to respectively include second and first plugs, the method further comprising:

detecting first light that passes through either a) a defect in the first plug or b) the at least one second channel end when the first plug is absent therefrom; and detecting second light that passes through either a) a defect in the second plug or b) the at least one first channel end when the second plug is absent therefrom.

11. The method of claim 9, wherein processing the first and second electrical detector signals includes detecting a reduction in intensity in one of the first and second light beams as compared to light intensities of the first and second light beams traveling through a defect-free channel so as to detect one of first and second defects in the form of material defects within the honeycomb structure.

12. A system for detecting defects in a ceramic filter body having a honeycomb structure with first and second ends and an array of longitudinal channels between the first and second ends and having respective first and second channel ends, the system comprising:

a first light source unit having multiple first light source elements and positioned adjacent the first honeycomb structure end, the first light source elements adapted to generate corresponding first light beams;

a first detector unit having multiple first detector elements per channel end for at least one first channel and positioned immediately adjacent the honeycomb structure second end so that multiple first light source elements and multiple first detector elements are capable of being in optical communication through the corresponding at least one first channel, the first detector unit configured to generate first electrical detector signals representative of a gray-scale variation in response to detecting first light from the first light beams; and a processor electrically connected to the first detector unit and adapted to process the first electrical detector signals to determine if at least one first defect exists within the at least one first channel.

13. The system of claim 12, wherein each channel has a channel width, and wherein:

the first light source unit comprises a linear array of the multiple first light source elements that generate the multiple first light beams; and the first detector unit comprises a contact sensor that spans multiple first channels and that has between 2 and 25 first detector elements per channel width.

14. The system of claim 12, further comprising:

a second light source unit having multiple second light source elements and positioned adjacent the honeycomb structure second end, the second light source elements adapted to generate a second light beams;

a second detector unit having multiple second detector elements per channel end for at least one second channel, and positioned adjacent the honeycomb structure first end so that the multiple second light source elements and the multiple second detector elements are capable of being in optical communication through the corresponding at least one second channel, the second detector unit configured to generate second electrical detector signals representative of a gray-scale variation in response to detecting second light from the second light beams; and the processor being electrically connected to the second detector unit and adapted to process the second electrical detector signals to determine if at least one second defect exists within the at least one second channel.

15. The system of claim 14, wherein the channels each have a channel width, and wherein:

the first and second light source units comprise respective first and second linear arrays having the respective first and second light source elements that generate respective multiple first and second light beams; and the first and second detector units comprise respective first and second contact sensors that span respective multiple first and second channels and that respectively have between 2 and 25 first and second detector elements per channel width.

16. The system of claim 12, wherein said at least one first defect includes one or more of:

a) one or more plug defects in plugs arranged in select channels at the second channel ends; and b) one or more material defects internal to the honeycomb structure.

17. A method of detecting defects in a ceramic honeycomb structure having first and second ends and an array of longitudinal channels having first and second channel ends, and ideally having first and second plugs at select first and second channel ends so as to seal the select channel ends, the method comprising:

transmitting first light through the first end to the second end through one or more first channels;

using multiple first detector elements per first channel end, at the second end, detecting first light that passes through at least one first defect to form a first gray-scale variation in the detected first light;

transmitting second light through the second end to the first end through one or more second channels;

using multiple second detector elements per second channel end at the first end, detecting second light that passes through at least one second defect to form a second gray-scale variation in the detected first light; and processing the first and second gray-scale variations to respectively detect the at least one first defect and the at least one second defect.

18. The method of claim 17, wherein detecting the first and second light is performed using respective first and second contact sensors that respectively include the multiple first and second detector elements, the first and second contact sensors being arranged at the second and first ends, respectively, including detecting the first light with the multiple first detector elements and detecting the second light with the multiple second detector elements.

19. The method of claim 17, wherein the at least one first defect and the at least one second defect respectfully include first and second missing plugs at the select first and second ends, respectively.

20. The method of claim 17, further comprising:
generating the first and second light using respective first and second linear light source units arranged adjacent the first and second ends, respectively;
detecting the first and second light using respective first and second linear detector units arranged adjacent the second and first ends, respectively, the first and second linear detector units respectively including the multiple first and second detector elements; and
moving either the first and second light source units and the first and second detector units relative to the honeycomb structure, or moving the honeycomb structure relative to the first and second light source units and the first and second detector units, to detect the at least one first defect and the at least one second defect over substantially the entire honeycomb structure.

* * * * *